US008017655B2

(12) United States Patent
Woodward et al.

(10) Patent No.: US 8,017,655 B2
(45) Date of Patent: Sep. 13, 2011

(54) NON-ACIDIC CYCLOPENTANE HEPTANOIC ACID, 2-CYCLOALKYL OR ARYLALKYL DERIVATIVES AS THERAPEUTIC AGENTS

(75) Inventors: David F. Woodward, El Toro, CA (US); Steven W. Andrews, Irvine, CA (US); Robert M. Burk, Irvine, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 67 days.

(21) Appl. No.: 12/339,494

(22) Filed: Dec. 19, 2008

(65) Prior Publication Data
US 2009/0227672 A1 Sep. 10, 2009

Related U.S. Application Data

(60) Continuation of application No. 10/282,726, filed on Oct. 28, 2002, now abandoned, which is a continuation of application No. 08/876,937, filed on Jun. 16, 1997, now abandoned, which is a continuation-in-part of application No. 08/371,339, filed on Jan. 11, 1995, now Pat. No. 5,607,978, which is a continuation of application No. 08/154,244, filed on Nov. 18, 1993, now abandoned, which is a division of application No. 07/948,056, filed on Sep. 21, 1992, now Pat. No. 5,352,708.

(51) Int. Cl.
*A61K 31/215* (2006.01)
*A61K 31/205* (2006.01)
*A61K 31/19* (2006.01)
*A61K 31/165* (2006.01)

(52) U.S. Cl. ........ 514/622; 514/530; 514/555; 514/570; 514/913; 560/55; 562/465; 564/171

(58) Field of Classification Search .................. 514/530, 514/555, 570, 913, 622; 560/55; 562/465; 564/171
See application file for complete search history.

(56) References Cited

U.S. PATENT DOCUMENTS

| | | | |
|---|---|---|---|
| 4,055,602 A | 10/1977 | Nelson | |
| 4,097,489 A | 6/1978 | Bundy | |
| 4,128,577 A | 12/1978 | Nelson | |
| 4,128,713 A | 12/1978 | Schneider | |
| 4,131,738 A | 12/1978 | Smith | |
| 4,171,331 A | 10/1979 | Biddlecom et al. | |
| 4,183,870 A | 1/1980 | Caton et al. | |
| 4,444,788 A | 4/1984 | Skuballa et al. | |
| 4,543,353 A | 9/1985 | Faustini et al. | |
| 4,599,353 A | 7/1986 | Bito | |
| 4,812,457 A | 3/1989 | Narumiya et al. | |
| 4,994,274 A | 2/1991 | Chan et al. | |
| 5,034,413 A | 7/1991 | Chan et al. | |
| 5,352,708 A | 10/1994 | Woodward et al. | |
| 5,414,016 A | 5/1995 | Skuballa et al. | |
| 5,422,368 A | 6/1995 | Stjernschantz et al. | |
| 5,510,383 A | 4/1996 | Bishop et al. | |
| 5,545,665 A | 8/1996 | Burk | |
| 5,587,391 A | 12/1996 | Burk | |
| 5,607,978 A | 3/1997 | Woodward et al. | |

FOREIGN PATENT DOCUMENTS

| | | |
|---|---|---|
| CA | 2 036 386 | 1/1991 |
| EP | 0 364 417 | 1/1989 |
| WO | WO 90/02553 | 3/1990 |
| WO | WO 92/08465 | 5/1992 |

OTHER PUBLICATIONS

Bito, L.Z.,"Prostaglandins and Related Compounds as Potential Ocular Therapeutic Agents", Biological Protection with Prostaglandins (Cohen, M.M., ed., Boc Raton, FL, CRC Press Inc., 1985, pp. 231-252.
Bito,L.Z., "Prostaglandins, Old Concepts and New Perspectives, " Arch Oph., vol. 105, Aug. 1987 p. 1036-1039.
Starr, M.S., "Further Studies on the Effect of Prostaglandin on Intraocular Pressure in the Rabbit", Exp. Eye Res., (1971) 170-177.
Nilsson, Siv F.E., et al, "PGF2a Increases Uveoscleral Outflow", ARVO Abstract, p. 284, Invest. Ophthalmol. Vis. Sci. 28 (supply) (1987).
Bito, L.Z.,"Prostaglandins, Other Eicosanoids, and Their Derivatives as Potential Antiglaucoma Agents", Applied Pharmacology in the Medical Treatment of Glaucoma, pp. 477-505,1984.
Declaration of Larry Wheeler, Ph.D.; Dec. 14, 2010.
Cantor LB, Hoop J, Wudunn D, Yung CW, Catoira Y, Valluri S, Cortes A, Acheampong A, Woodward DF, Wheeler LA. Levels of bimatoprost acid in the aqueous humour after bimatoprost treatment of patients with cataract. Br J Ophthalmol. May 2007;91(5):629-32. Epub Nov. 29, 2006.
Davies SS, Ju WK, Neufeld AH, Abran D, Chemtob S, Roberts LJ II. Hydrolysis of bimatoprost (Lumigan) to its free acid by ocular tissue in vitro. J Ocul Pharmacol Ther. Feb. 2003;19(1):45-54.
Camras CB, Toris CB, Sjoquist B, Milleson M, Thorngren JO, Hejkal TW, Patel N, Barnett EM, Smolyak R, Hasan SF, Hellman C, Meza JL, Wax MB, Stjernschantz J. Detection of the free acid of bimatoprost in aqueous humor samples from human eyes treated with bimatoprost before cataract surgery. Ophthalmology. Dec. 2004;111(12):2193-8.
Faulkner R, Sharif NA, Orr S, Sall K, Dubiner H, Whitson JT, Moster M, Craven ER, Curtis M, Pailliotet C, Martens K, Dahlin D. Aqueous humor concentrations of bimatoprost free acid, bimatoprost and travoprost free acid in cataract surgical patients administered multiple topical ocular doses of LUMIGAN or TRAVATAN. J Ocul Pharmacol Ther. Apr. 2010;26(2):147-56.

(Continued)

*Primary Examiner* — Peter G O'Sullivan
(74) *Attorney, Agent, or Firm* — John E. Wurst; Kevin J. Forrestal; Doina G. Ene (57) ABSTRACT

The present invention provides cyclopentane heptanoic acid, 2-cycloalkyl or arylalkyl compounds, which may be substituted in the 1-position with amino, amido, ether or ester groups, e.g., a 1-OH cyclopentane heptanoic acid, 2-(cycloalkyl or arylalkyl) compound. The cyclopentane heptanoic acid, 2-(cycloalkyl or arylalkyl) compounds of the present invention are potent ocular hypotensives, and are particularly suitable for the management of glaucoma. Moreover, the cyclopentane heptanoic, 2-(cycloalkyl or arylalkyl) compounds of this invention are smooth muscle relaxants with broad application in systemic hypertensive and pulmonary diseases; smooth muscle relaxants with application in gastrointestinal disease, reproduction, fertility, incontinence, shock, etc.

6 Claims, 3 Drawing Sheets

OTHER PUBLICATIONS

Maxey KM, Johnson JL, Labrecque J. The hydrolysis of bimatoprost in corneal tissue generates a potent prostanoid FP receptor agonist. Surv Ophthalmol. Aug. 2002;47 Suppl 1:S34-40.

Bean GW, Camras CB. Commercially available prostaglandin analogs for the reduction of intraocular pressure: similarities and differences. Surv Ophthalmol. Nov. 2008;53.

Camras CB, Sharif NA, Wax MB, Stjernschantz J. Bimatoprost, the prodrug of a prostaglandin analogue. Br J Ophthalmol. Jun. 2008;92(6):862-3.

Romano MR, Lograno MD. Evidence for the involvement of cannabinoid CB1 receptors in the bimatoprost-induced contractions on the human isolated ciliary muscle. Invest Ophthalmol Vis Sci. Aug. 2007;48(8):3677-82.

Sharif NA, Kelly CR, Crider JY, Williams GW, Xu SX. Ocular hypotensive FP prostaglandin (PG) analogs: PG receptor subtype binding affinities and selectivities, and agonist potencies at FP and other PG receptors in cultured cells. J Ocul Pharmacol Ther. Dec. 2003;19(6):501-15.

Sharif NA, Klimko, P. Update and commentary on the pro-drug bimatoprost and a putative 'prostamide receptor'. Expert Review of Ophthalmology. Oct. 2009;4(5):477-489.

Alm A, Nilsson SF. Uveoscleral Outflow—A Review. Exp Eye Res. Apr. 2009: 88(4) 760-8. Epub Jan. 3, 2009.

Woodward DF, Krauss AH, Nilsson SFE. Bimatoprost Effects on Aqueous Humor Dynamics in Monkeys. J Ophthalmol. 2010: Article ID 926192, 5 pages.

Sjöquist B, Johansson A, Stjernschantz J. Pharmacokinetics of latanoprost in the cynomolgus monkey. 3rd communication: tissue distribution after topical administration on the eye studied by whole body autoradiography, Glaucoma research laboratories. Arzneim-Forsch/Drug Res 1999:49:240-249.

Woodward DF, Krauss AH, Chen J, et al: The pharmacology of bimatoprost (Lumigan). Surv Ophthalmol 45(Suppl 4): S337-45, 2001.

Woodward DF, Phelps RL, Krauss AH, Weber A, Short B, Chen J, Liang Y, Wheeler LA. Bimatoprost: a novel antiglaucoma agent. Cardiovasc Drug Rev. 2004 Summer;22(2):103-20.

Katz LJ, Ichhpujani P, Hollo G et al. Comparison of Human Ocular Distribution of Bimatoprost and Latanoprost. 2010 (manuscript submitted).

Woodward DF, Krauss AH, Chen J, et al. Pharmacological characterization of a novel anti-glaucoma agent. J. Pharmacol. Exp. Ther. 305:772-85, 2003.

Frenkel RE, Noecker RJ, Craven ER. Evaluation of circadian control of intraocular pressure after a single drop of bimatoprost 0.03% or travoprost 0.004%. Curr Med Res Opin. Apr. 2008;24(4):919-23. Epub Feb 8, 2008.

Hellberg MR, KE T-L, Haggard K, et al: The hydrolysis of the prostaglandin analog prodrug bimatoprost to 17-phenyltrinor PGF2a by human and rabbit ocular tissue. J Ocular Pharmacol Ther 19:97-103, 2003.

Sjöquist B, Stjernschantz J. Ocular and systemic pharmacokinetics of latanoprost in humans. Surv Ophthalmol. Aug. 2002;47 (Supp 1):S6-12.

Cantor LB. Reply—Bimatoprost, the prodrug of a prostaglandin analogue. Br J Ophthalmol 2008;92:863-864.

Sharif NA, Kelly CR, Crider JY. Human trabecular meshwork cell responses induced by bimatoprost, travoprost, unoprostone, and other FP prostaglandin receptor agonist analogues. Invest Ophthalmol Vis Sci 2003;44:715-21.

Sharif NA, Crider JY, Husain S, et al. Human ciliary muscle cell responses to FP-class prostaglandin analogs: phosphoinositide hydrolysis, intracellular Ca2+ mobilization and MAP kinase activation. J Ocul Pharmacol Ther 2003;19:437-55.

Stamer WD, Piwnica D, Jolas T, Carling RW, Cornell CL, Fliri H, Martos J, Pettit SN, Wang JW, Woodward DF. Cellular basis for bimatoprost effects on human conventional outflow. Invest Ophthalmol Vis Sci. Oct. 2010;51(10):5176-81. Epub Apr 30, 2010.

Resul B, Stjernschantz J, No K, Liljebris C, Selen G, Astin M, Karlsson M, Bito LZ. Phenyl-substituted prostaglandins: potent and selective antiglaucoma agents. J Med Chem. Jan. 22, 1993;36(2):243-8.

Stjernschantz J. Studies on ocular inflammation and development of a prostaglandin analogue for glaucoma treatment. Exp Eye Res. Apr. 2004;78(4):759-66.

Stjernschantz JW. From PGF2α-isopropyl ester to latanoprost: a review of the development of Xalatan: the Proctor Lecture. Invest Ophthalmol Vis Sci. May 2001;42(6):1134-45.

FDA Label for Approved NDA 22-184 of Lumigan 0.01% and Lumigan 0.03%, Aug. 31, 2010.

Sharif NA, Kaddour-Djebbar I, Abdel-Latif AA. Cat iris sphincter smooth-muscle contraction: comparison of FP-class prostaglandin analog agonist activities. J Ocul Pharmacol Ther. Apr. 2008;24(2):152-63.

Spada CS, Krauss AH, Woodward DF, Chen J, Protzman CE, Nieves AL, Wheeler LA, Scott DF, Sachs G. Bimatoprost and prostaglandin F(2 alpha) selectively stimulate intracellular calcium signaling in different cat iris sphincter cells. Exp Eye Res. Jan. 2005;80(1):135-45.

Woodward, D.F., Krauss, A.H., Wang, J.W., Protzman, C.E., Nieves, A.L., Liang, Y., Donde, Y., Burk, R.M., Landsverk, K., Struble, C. "Identification of an antagonist that selectively blocks the activity of prostamides (prostaglandin ethanolamides) in the feline iris." Br. J. Pharmacol. 150:342-352 (2007).

Liang, Y., Woodward, D.F., Guzman, V.M., LI, C., Scott, D.F., Wang, J.W., et al. (2008). "Identification and pharmacological characterization of the prostaglandin FP receptor and FP receptor variant complexes." Br. J. Pharmacol. 154: 1079-1093.

Van Alphen Gwhm, Wilhelm PB, Elsenfeld PW. The effect of prostaglandins on the isolated internal muscles of the mammalian eye, including man. Documenta Ophthalmologica, 1976, vol. 42, No. 2, pp. 397-415.

Poyer JF, Millar C, Kaufman PL. Prostaglandin F2 alpha effects on isolated rhesus monkey ciliary muscle. Invest Ophthalmol Vis Sci. Nov. 1995;36(12):2461-5.

Yamaji K, Yoshitomi T, Ishikawa H, Usui S. Prostaglandins E1 and E2, but not F2alpha or latanoprost, inhibit monkey ciliary muscle contraction. Curr Eye Res. Aug. 2005;30(8):661-5.

Berglund BA, Boring DL, Howlett AC. Investigation of structural analogs of prostaglandin amides for binding to and activation of CB1 and CB2 cannabinoid receptors in rat brain and human tonsils. Adv Exp Med Biol. 1999;469:527-33.

Cadet P, Mantione KJ, Stefano GB. Molecular identification and functional expression of mu 3, a novel alternatively spliced variant of the human mu opiate receptor gene. J Immunol. May 15, 2003;170(10):5118-23.

Vielhauer GA, Fujino H, Regan JW. Cloning and localization of hFP(S): a six-transmembrane mRNA splice variant of the human FP prostanoid receptor. Arch Biochem Biophys. Jan. 15, 2004;421(2):175-85.

Jordan BA, Devi LA. G-protein-coupled receptor heterodimerization modulates receptor function. Nature. Jun. 17, 1999;399(6737):697-700.

White JH, Wise A, Main MJ, Green A, Fraser NJ, Disney GH, Barnes AA, Emson P, Foord SM, Marshall FH. Heterodimerization is required for the formation of a functional GABA(B) receptor. Nature. Dec. 17, 1998;396(6712):679-82.

Wilson SJ, Roche AM, Kostetskaia E, Smyth EM. Dimerization of the human receptors for prostacyclin and thromboxane facilitates thromboxane receptor-mediated cAMP generation. J Biol Chem. Dec. 17, 2004;279(51):53036-47. Epub Oct. 7, 2004.

Crowston et al. Effect of Bimatoprost on Intraocular Pressure in Prostaglandin FP Receptor Knockout Mice. Investigative Ophthalmology and Visual Science, 46:4571-77 (2005).

Response from the Food and Drug Administration to Pfizer's Citizen Petition and a Supplement (Aug. 31, 2010) at 23 (Exhibit 5).

Complaint For Patent Infringment: Civil Action No. 1:10-CV-681; Allergan, Inc. And Duke University V. Apotex Inc. And Apotex Corp.; Filed Sep. 8, 2010.

Answer, Defences and Counterclaims of Defendants Apotex Inc. and Apotex Corp,. Civil Action No. 10-CV-681; *Allergan, Inc. and Duke University* v. *Apotex Inc. and Apotex Corp.*

Fig. 2.

NON-ACIDIC CYCLOPENTANE HEPTANOIC ACID, 2-CYCLOALKYL OR ARYLALKYL DERIVATIVES AS THERAPEUTIC AGENTS

CROSS REFERENCE TO RELATED APPLICATIONS

This application is a Continuation of U.S. patent application Ser. No. 10/282,726, filed Oct. 28, 2002, now abandoned, which is a continuation of U.S. patent application Ser. No. 08/876,937, filed on Jun. 16, 1997, now abandoned, which is a continuation-in-part of U.S. patent application Ser. No. 08/371,339, filed on Jan. 11, 1995, now U.S. Pat. No. 5,607,978, which is a continuation of U.S. patent application Ser. No. 08/154,244 which was filed on Nov. 18, 1993, now abandoned, which is a divisional of U.S. patent application Ser. No. 07/948,056, filed on Sep. 21, 1992, now U.S. Pat. No. 5,352,708 issued on Oct. 4, 1994, all of which are hereby incorporated by reference.

BACKGROUND OF THE INVENTION

1. Field of the Invention

The present invention provides cyclopentane heptanoic acid, 2-cycloalkyl or arylalkyl compounds, which may be substituted in the 1-position with amino, amido, ether or ester groups, e.g., a 1-OH cyclopentane heptanoic acid, 2-(cycloalkyl or arylalkyl) compound. The cyclopentane heptanoic acid, 2-(cycloalkyl or arylalkyl) compounds of the present invention are potent ocular hypotensives, and are particularly suitable for the management of glaucoma. Moreover, the cyclopentane heptanoic, 2-(cycloalkyl or arylalkyl) compounds of this invention are smooth muscle relaxants with broad application in systemic hypertensive and pulmonary diseases; smooth muscle relaxants with application in gastrointestinal disease, reproduction, fertility, incontinence, shock, etc.

2. Description of the Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S. *Exp. Eye Res.* 1971, 11, pp. 170-177; Bito, L. Z. *Biological Protection with Prostaglandins* Cohen, M. M., ed., Boca Raton, Fla., CRC Press Inc., 1985, pp. 231-252; and Bito, L. Z., *Applied Pharmacology in the Medical Treatment of Glaucomas* Drance, S. M. and Neufeld, A. H. eds., New York, Grune & Stratton, 1984, pp. 477-505). Such prostaglandins include $PGF_{2a}$, $PGF_{1a}$, $PGE_2$, and certain lipid-soluble esters, such as $C_1$ to $C_5$ alkyl esters, e.g. 1-isopropyl ester, of such compounds.

In the U.S. Pat. No. 4,599,353 certain prostaglandins, in particular $PGE_2$ and $PGF_{2a}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., *Invest. Opthalmol. Vis. Sci.* 28(suppl), 284 (1987)].

The isopropyl ester of $PGF_{2a}$ has been shown to have significantly greater hypotensive potency than the parent compound, which was attributed to its more effective penetration through the cornea. In 1987 this compound was described as "the most potent ocular hypotensive agent ever reported." [See, for example, Bito, L. Z., *Arch. Ophthalmol.* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2a}$ and its prodrugs, e.g. its 1-isopropyl ester, in humans. The clinical potential of prostaglandins in the management of conditions associated with increased ocular pressure, e.g. glaucoma, is greatly limited by these side effects.

Certain phenyl and phenoxy mono, tri and tetra nor prostaglandins and their 1-esters are disclosed in European Patent Application 0,364,417 as useful in the treatment of glaucoma or ocular hypertension.

In a series of co-pending United States patent applications assigned to Allergan, Inc. prostaglandin esters with increased ocular hypotensive activity accompanied with no or substantially reduced side-effects are disclosed. The co-pending U.S. Ser. No. 386,835 (filed 27 Jul. 1989), relates to certain 11-acyl-prostaglandins, such as 11-pivaloyl, 11-acetyl, 11-isobutyryl, 11-valeryl, and 11-isovaleryl $PGF_{2a}$. Intraocular pressure reducing 15-acyl prostaglandins are disclosed in the co-pending application U.S. Ser. No. 357,394 (filed 25 May 1989). Similarly, 11,15-9,15- and 9,11-diesters of prostaglandins, for example 11,15-dipivaloyl $PGF_{2a}$ are known to have ocular hypotensive activity. See the patent applications U.S. Ser. No. 385,645 filed 27 Jul. 1990, now U.S. Pat. No.

4,494,274; U.S. Ser. No. 584,370 which is a continuation of U.S. Ser. No. 386,312, and Ser. No. 585,284, now U.S. Pat. No. 5,034,413 which is a continuation of U.S. Ser. No. 386,834, where the parent applications were filed on 27 Jul. 1989. The disclosures of these patent applications are hereby expressly incorporated by reference.

SUMMARY OF THE INVENTION

We have found that certain cyclopentane heptanoic acid, 2-cycloalkyl or arylalkyl compounds and derivatives thereof wherein the carboxylic acid group is replaced by a non-acidic substituent have pronounced effects on smooth muscle and are potent ocular hypotensive agents. We have further found that such compounds, in certain instances, may be significantly more potent than their respective parent compounds and, in the case of glaucoma surprisingly, cause no or significantly lower ocular surface hyperemia than the parent compounds.

The present invention relates to methods of treating cardiovascular, pulmonary-respiratory, gastrointestinal, reproductive, allergic disease, shock and ocular hypertension which comprises administering an effective amount of a cyclopentane heptanoic acid, 2-cycloalkyl or arylalkyl compound represented by the formula I wherein the dashed bonds represent a single or double bond which can be in the cis or trans configuration, A is an alkylene or alkenylene radical having from two to six carbon atoms, which radical may be interrupted by one or more oxide radicals and substituted with one or more hydroxy, oxo, alkyloxy or alkylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is a radical selected from the group consisting of $-OR^4$ and $-N(R^4)_2$ wherein $R^4$ is selected from the group consisting of hydrogen, a lower alkyl radical having from one to six carbon atoms, wherein $R^5$ is a lower alkyl radical having from one to six carbon atoms; Z is $=O$ or represents 2 hydrogen radicals; one of $R_1$ and $R_2$ is $=O$, $-OH$ or a $-O(CO)R_6$ group, and the other one is $-OH$ or $-O(CO)R_6$, or $R_1$ is $=O$ and $R_2$ is H, wherein $R_6$ is a saturated or unsaturated acyclic hydrocarbon group having from 1 to about 20 carbon atoms, or $-(CH_2)mR_7$ wherein m is 0 or an integer of from 1 to 10, and $R_7$ is cycloalkyl radical, having from three to seven carbon atoms, or a hydrocarbyl aryl or heteroaryl radical, as defined above, or a pharmaceutically-acceptable salt thereof, provided, however, that when B is not substituted with a pendant heteroatom-containing radical, and Z is $=O$, then X is not $-OR^4$. (That is, the cycloalkyl or hydrocarbyl aryl or heteroaryl radical is not substituted with a pendant radical having an atom other than carbon or hydrogen.)

More preferably the method of the present invention comprises administering a cyclopentane heptanoic acid, 2-(phenyl alkyl or phenyloxyalkyl) represented by the formula II wherein y is 0 or 1, x is 0 or 1 and x and y are not both 1, Y is a radical selected from the group consisting of alkyl, halo, e.g. fluoro, chloro, etc., nitro, amino, thiol, hydroxy, alkyloxy, alkylcarboxy, halo substituted alkyl wherein said alkyl radical comprises from one to six carbon atoms, etc. and n is 0 or an integer of from 1 to about 3 and $R_3$ is $=O$, $-OH$ or $-O(CO)R_6$ wherein $R_6$ is as defined above. Preferably, n is 1 or 2.

Preferably the compound used in the above method of treatment is a compound of formula (III).

wherein hatched lines indicate a configuration, solid triangles are used to indicate β configuration

In another aspect, the present invention relates to a method of treating cardiovascular, pulmonary-respiratory, gastrointestinal, reproductive and allergic diseases, shock and ocular hypertension which comprises administering to a subject a pharmaceutical composition comprising a therapeutically effective amount of a compound of formula (IV)

wherein $Y^1$ is Cl or trifluoromethyl and the other symbols and substituents are as defined above, in combination with a pharmaceutical carrier.

Finally, the method of the present invention relates to a method of treating cardiovascular, pulmonary-respiratory, gastrointestinal, reproductive and allergic diseases, shock and ocular hypertension which comprises administering to a subject a pharmaceutical composition comprising a therapeutically effective amount of a compound of Formula V and the 9- and/or 11- and/or 15 esters thereof.

In a further aspect, the present invention relates to pharmaceutical compositions comprising a therapeutically effective amount of a compound of formulae (I), (II), (III), (IV) or (V) wherein the symbols have the above meanings, or a pharmaceutically acceptable salt thereof in admixture with a non-toxic, pharmaceutically acceptable liquid vehicle.

In a still further aspect, the present invention relates to cyclopentane heptanoic acid, 2-cycloalkyl or arylalkyl compounds of the above formulae, wherein the substituents and symbols are as defined hereinabove, or a pharmaceutically acceptable salt of such compounds.

wherein the substituents and symbols are as hereinabove defined. More preferably the compounds are represented by formula (III).

Figure 1:
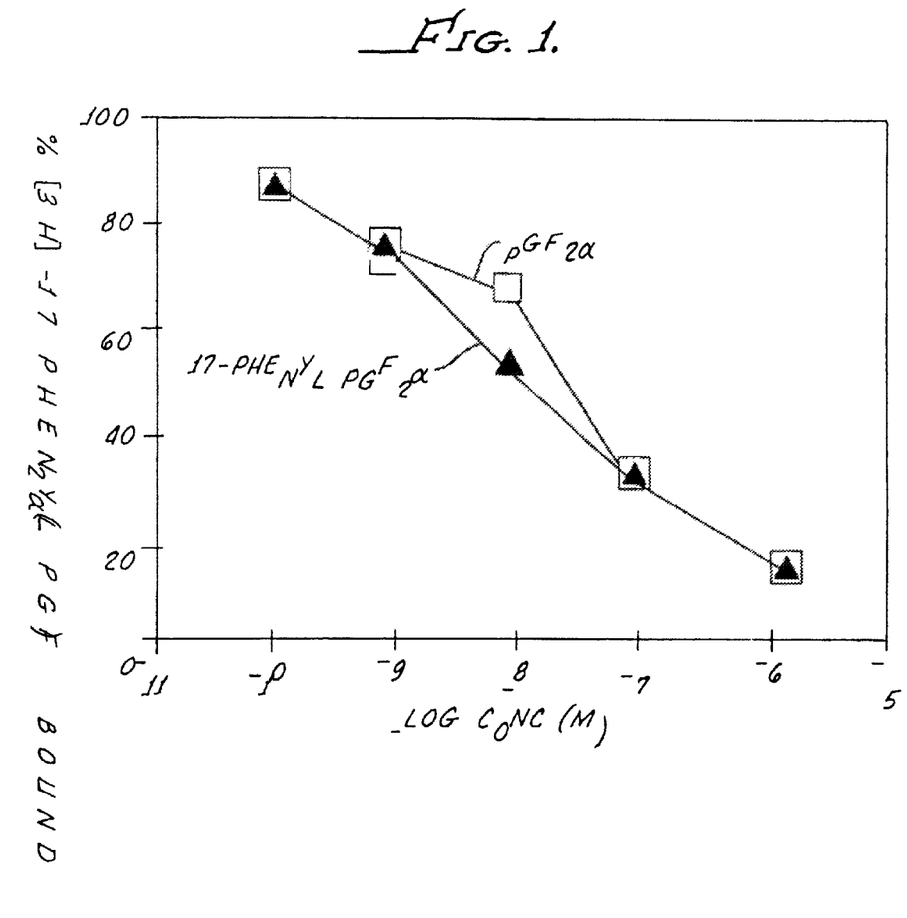
FIG. 1. refers to inhibition of 3H-17-phenylPGF2α specific binding to membranes obtained for rat colon while competition by unlabeled 17-phenyl PGF2α and PGF2α are represented by filled triangles and open squares, respectively.
Figure 2:
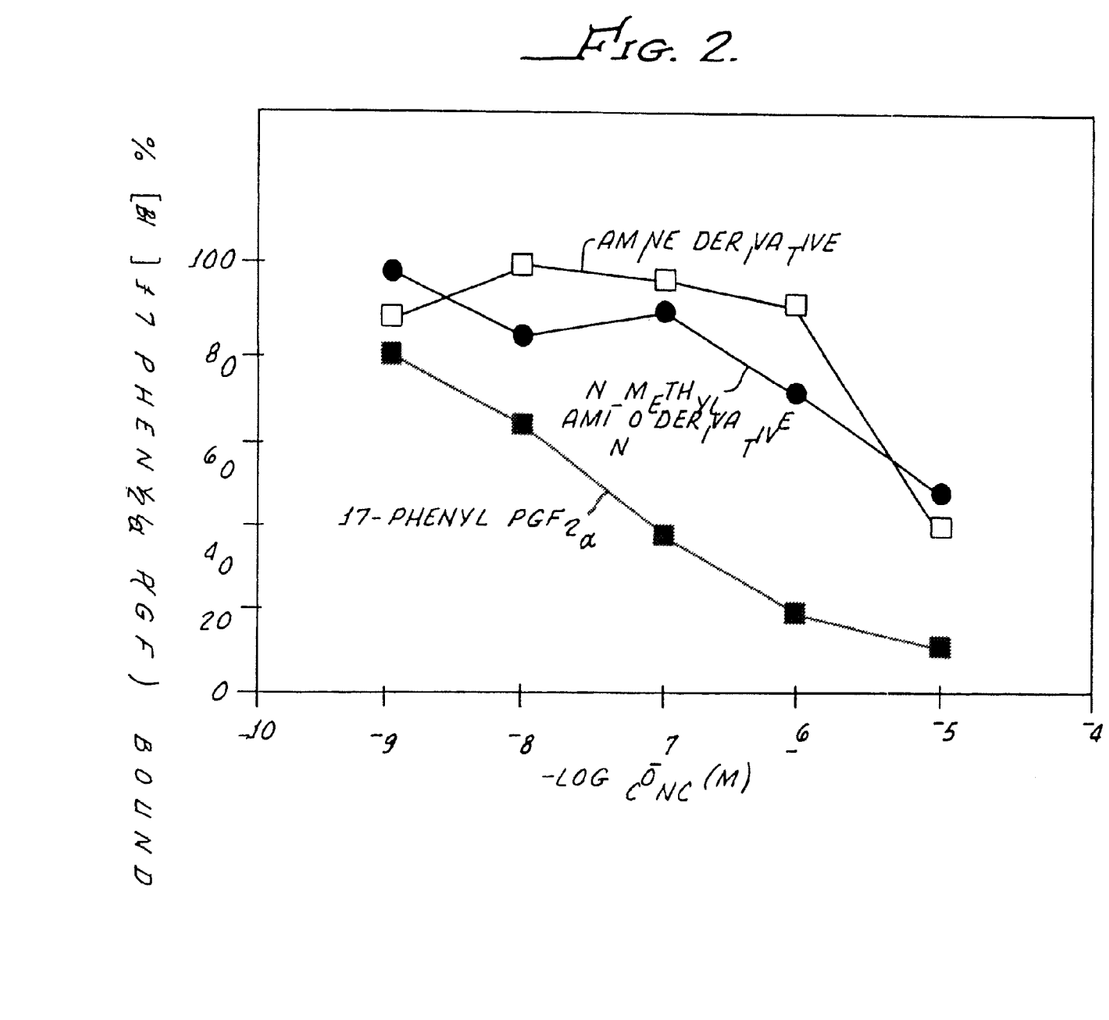
FIG. 2. refers to inhibition of 3H-17-phenylPGF2α specific binding to membranes obtained for rat colon while competition by unlabeled 17-phenyl PGF2α-amine -17phenyPGF2α-N-methyl amine, and 17-phenyl PGF2α are represented by filled squares, open squares, and filled circles, respectively.
Figure 3:
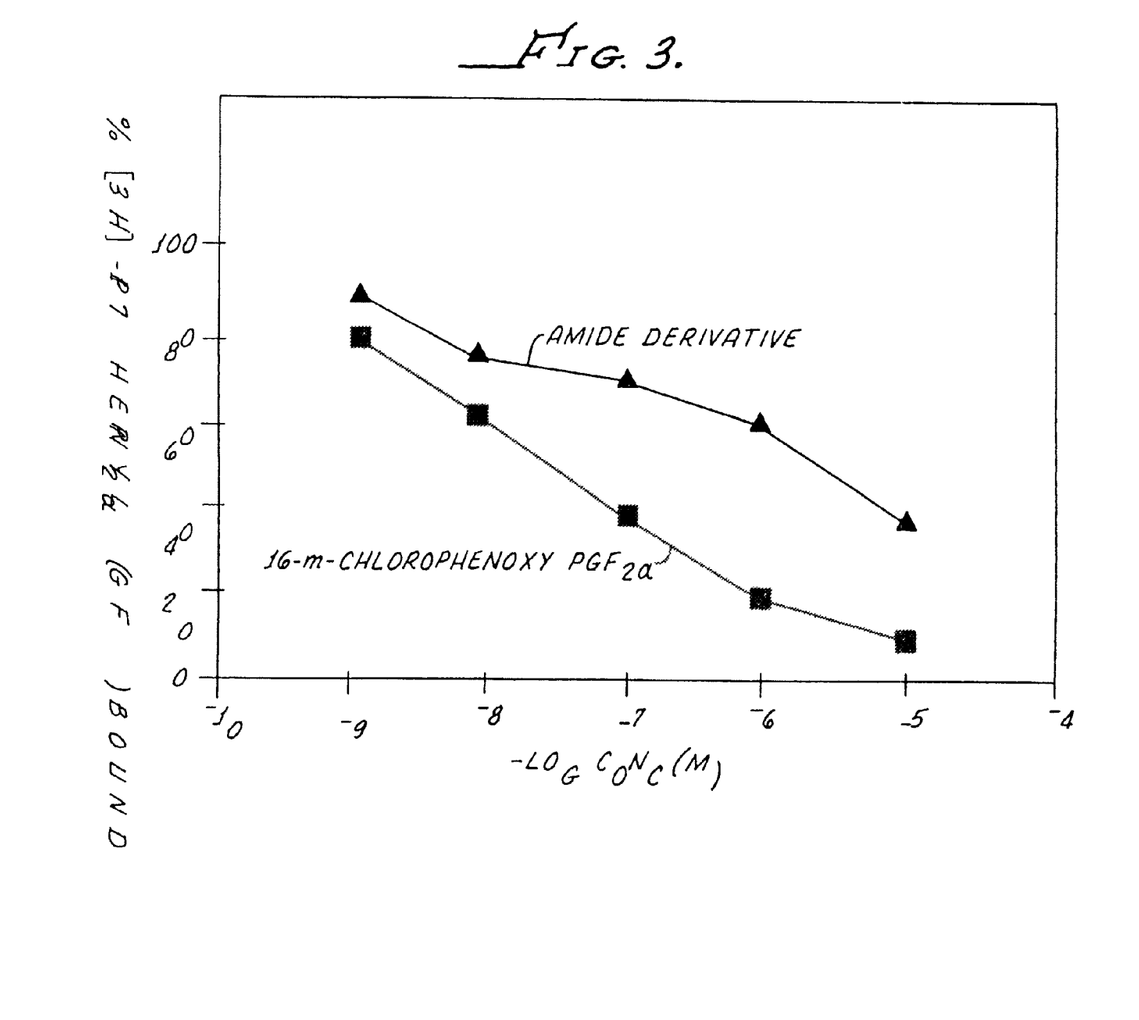
FIG. 3. refers to inhibition of 3H-17-phenylPGF2α specific binding to membranes obtained for rat colon while competition by unlabeled 16-m-chlorophenoxy PGF2α and its amide derivative are represented by filled squares and triangles, respectively.

wherein the substituents and symbols are as defined above. More preferably, the compounds utilized in the present invention are compounds represented by the formula (IV)

wherein the substituents and the symbols are as defined above.

Most preferably the present invention utilizes the novel compounds of the formula (V)

DETAILED DESCRIPTION OF THE INVENTION

The present invention relates to the use of cyclopentane heptanoic acid, 2-cycloalkyl or arylalkyl compounds as therapeutic agents, e.g. as ocular hypotensives. These therapeutic agents are represented by compounds having the formula I, as defined above. The preferred nonacidic cyclopentane heptanoic acid, 2-(phenyl alkyl or phenyloxyalkyl) compounds used in accordance with the present invention are encompassed by the following structural formula (II)

and their 9- and/or 11- and/or 15-esters.

In all of the above formulae, as well as in those provided hereinafter, the dotted lines on bonds between carbons 5 and 6 (C-5), between carbons 13 and 14 (C-13), between carbons 8 and 12 (C-8), and between carbons 10 and 11 (C-10) indicate a single or a double bond which can be in the cis or trans configuration. If two solid lines are used that indicates a specific configuration for that double bond. Hatched lines at positions C-9, C-11 and C-15 indicate the α configuration. If one were to draw the β configuration, a solid triangular line would be used.

In the compounds used in accordance with the present invention, compounds having the C-9 or C-11 or C-15 substituents in the α or β configuration are contemplated. As hereinabove mentioned, in all formulas provided herein bro- ken line attachments to the cyclopentane ring indicate substituents in the a configuration. Thickened solid line attachments to the cyclopentane ring indicate substituents in the β configuration. Also, the broken line attachment of the hydroxyl group or other substituent to the C-11 and C-15 carbon atoms signifies the α configuration.

For the purpose of this invention, unless further limited, the term "alkyl" refers to alkyl groups having from one to ten carbon atoms, the term "cycloalkyl" refers to cycloalkyl groups having from three to seven carbon atoms, the term "aryl" refers to aryl groups having from four to ten carbon atoms. The term "saturated or unsaturated acyclic hydrocarbon group" is used to refer to straight or branched chain, saturated or unsaturated hydrocarbon groups having from one to about 6, preferably one to about 4 carbon atoms. Such groups include alkyl, alkenyl and alkynyl groups of appropriate lengths, and preferably are alkyl, e.g. methyl, ethyl, propyl, butyl, pentyl, or hexyl, or an isomeric form thereof.

The definition of $R_6$ may include a cyclic component, $-(CH_2)_m R_7$, wherein n is 0 or an integer of from 1 to 10, $R_7$ is an aliphatic ring from about 3 to about 7 carbon atoms, or an aromatic or heteroaromatic ring. The "aliphatic ring" may be saturated or unsaturated, and preferably is a saturated ring having 3-7 carbon atoms, inclusive. As an aromatic ring, $R_7$ preferably is phenyl, and the heteroaromatic rings have oxygen, nitrogen or sulfur as a heteroatom, i.e. $R_7$ may be thienyl, furanyl, pyridyl, etc. Preferably m is 0 or an integer of from 1 to 4.

Z is =O or represents two hydrogen atoms.

X may be selected from the group consisting of $-OR^4$ and $-N(R^4)_2$ wherein $R^4$ is selected from the group consisting of hydrogen, a lower alkyl radical having from one to six carbon atoms, wherein $R^5$ is a lower alkyl radical having from one to six carbon atoms.

Preferred representatives of the compounds within the scope of the present invention are the compounds of formula V wherein X is —OH, i.e. cyclopentane heptenoic acid, 5-cis-2-(3-α hydroxy-4-m-chlorophenoxy-1-trans-butenyl)-3,5-dihydroxy, [$1_α$, $2_β$, $3_α$, $5_α$] and cyclopentane methylheptenoate-5-cis-2(3-αhydroxy-4-m-chlorophenoxy-1-trans-butenyl)-3,5 dihydroxy, [$1_α$,$2_β$,$3_α$,$5_α$] and the 9- and/or 11- and/or 15-esters of this compound. (The numbered designations in brackets refer to the positions on the cyclopentane ring.)

The following novel compounds may be used in the pharmaceutical compositions and the methods of treatment of the present invention.

(1) cyclopentane heptenol-5-cis-2-(3α-hydroxy-5-phenyl-1-trans-pentenyl)-3,5-dihydroxy, [$1_α$, $2_β$, $3_α$, $5_α$]

(2) cyclopentane heptenamide-5-cis-2-(3α-hydroxy-5-phenyl-1-trans-pentenyl)-3, 5-dihydroxy, [$1_α$, $2_β$, $3_α$, $5_α$]

(3) cyclopentane N,N-dimethylheptenamide-5-cis-2-(3α-hydroxy-5-phenyl-1-trans-pentenyl)-3,5-dihydroxy, [$1_α$, $2_β$, $3_α$, $5_α$]

(4) cyclopentane heptenyl methoxide-5-cis-2-(3α-hydroxy-5-phenyl-1-trans-pentenyl)-3,5-dihydroxy, [$1_α$, $2_β$, $3_α$, $5_α$]

(5) cyclopentane heptenyl ethoxide-5-cis-2-(3α-hydroxy-4-meta-chlorophenoxy-1-trans-pentenyl)-3,5-dihydroxy, [$1_α$, $2_β$, $3_α$, $5_α$]

(6) cyclopentane heptenylamide-5-cis-2-(3α-hydroxy-4-meta-chlorophenoxy-1-trans-pentenyl)-3,5-dihydroxy, [$1_α$, $2_β$, $3_α$, $5_α$]

(7) cyclopentane heptenylamide-5-cis-2-(3α-hydroxy-4-trifluoromethylphenoxy-1-trans-pentenyl)-3,5-dihydroxy, [$1_α$, $2_β$, $3_α$, $5_α$]

(8) cyclopentane N-isopropyl heptenamide-5-cis-2-(3α-hydroxy-5-phenyl-1-trans-pentenyl)-3,5-dihydroxy, [$1_α$, $2_β$, $3_α$, $5_α$]

(9) cyclopentane N-ethyl heptenamide-5-cis-2-(3α-hydroxy-5-phenyl-1-trans-pentenyl)-3,5 dihydroxy, [$1_α$, $2_β$, $3_α$, $5_α$]

(10) cyclopentane N-methyl heptenamide-5-cis-2-(3α-hydroxy-5-phenyl-1-trans-pentenyl)-3,5-dihydroxy, [$1_α$, $2_β$, $3_α$, $5_α$]

(11) cyclopentane heptenol-5-cis-2-(3α-hydroxy-4-meta-chlorophenoxy-1-trans-butenyl)-3,5-dihydroxy, [$1_α$, $2_β$, $3_α$, $5_α$]

(12) cyclopentane heptenamide-5-cis-2-(3α-hydroxy-4-meta-chlorophenoxy-1-trans-butenyl)-3,5-dihydroxy, [$1_α$, $2_β$, $3_α$, $5_α$]

(13) cyclopentane heptenol-5-cis-2-(3α-hydroxy-5-phenyl-1-trans-pentenyl)3,5-dihydroxy, [$1_α$, $2_β$, $3_α$, $5_α$]

A pharmaceutically acceptable salt is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, etc.

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 ml.

The invention is further illustrated by the following non-limiting Examples.

Example 1

Cyclopentane heptenoic acid, 5-cis-2-(3α-hydroxy-4-m-chlorophenoxy-1-trans-butenyl)-3,5-dihydroxy, [$1_\alpha$, $2_\beta$, $3_\alpha$, $5_\alpha$]

This compound may be purchased from Cayman Chemical Company of Ann Arbor, Mich. or synthesized by methods known in the art.

Example 2

Cyclopentane methylheptenoate-5-cis-2 (3α-hydroxy-4-m-chlorophenoxy-1-trans-butenyl)-3,5-dihydroxy, [$1_\alpha$, $2_\beta$, $3_\alpha$, $5_\alpha$]

To a stirred solution of cyclopentane heptenoic acid, 5-cis-2-(3α-hydroxy-4-m-chlorophenoxy-1-trans-butenyl)-3,5-dihydroxy, [$1_\alpha$, $2_\beta$, $3_\alpha$, $5_\alpha$](24 mg. 0.0565 mmol) in acetone (0.6 ml) at room temperature was added 1,8-diazabicyclo [5.4.0.] undec-7-ene (DBU) (40, ul, 0.27 mmol) and methyl iodide (20 ul, 0.32 mmol). The reaction turned yellow with the DBU addition. The reaction was maintained at room temperature for 6.5 hours, then was diluted with ethyl acetate (30 ml) and filtered through a plug of celite with the aid of ethyl acetate. After concentration in vacuo, the residue was flushed with ethylacetate (EtOAc) through a 20 mm×160 mm column of silica to give the desired methyl ester.

Example 3

Cyclopentane heptenamide-5-cis-2-(3α-hydroxy-4-m-chlorophenoxy-1-trans-butenyl)-3,5-dihydroxy, [1α, 2β, 3α, 5α]

A mixture of the methyl ester of the compound of Example 1 (9.2 mg, 0.0222 mmol) and $NH_4Cl$ (10 mg, 0.187 mmol) in $NH_3$ was heated at 80° C. for 12 hours. After cooling to room temperature, the solvents were evaporated and the residue was subjected to column chromatography to provide the named amide as 7.2 mg of a clear, colorless liquid.

Example 4

Cyclopentane heptenoic acid-5-cis2-(3α-hydroxyl-4-m-trifluoromethylphenoxy-1-trans-butenyl)-3,5-dihydroxy [1α, 2β, 3α, 5α

This compound may be purchased from Cayman Chemical Company of Ann Arbor, Mich. or synthesized by methods known in the art.

Example 5

Cyclopentane heptenamide-5-cis2-(3α-hydroxyl-4-m-trifluoromethylphenoxy-1-trans-butenyl)-3,5-dihydroxy [1α, 2β, 3α, 5α

A mixture of the methyl ester of the compound of Example 4 (fluprostenol) and $NH_4Cl$ in $NH_3$ is heated at 80° C. for 12 hours. After cooling to room temperature the solvents are evaporated and the residue is subjected to column chromatography to provide the named amide.

Example 6

Measurement of intraocular pressure studies in dogs involved pneumatonometry performed in conscious, Beagle dogs of both sexes (10-15 kg). The animals remained conscious throughout the study and were gently restrained by hand. Drugs were administered topically to one eye as a 25 μL volume drop, the other eye received 25 μ: vehicle (0.1% polysorbate 80:10 mM TRIS) as a control. 0.1% proparacaine was used for corneal anesthesia during tonometry. Intraocular pressure was determined just before drug administration and at 2, 4 and 6 hour thereafter on each day of the 5 day study. Drug was administered twice a day, with a 6 hour interval between doses that spanned the intraocular pressure measurement time frame. The result reported in Table 1, below.

TABLE 1

Comparison of effects of certain compounds of the invention on dog intraocular pressure. Values indicate mean changes from baseline introcular pressure (±SEM) at predetermined times post-dosing.

INTRAOCULAR PRESSURE (mmHg) CHANGE AT PREDETERMINED TIMES (HR)

| COMPOUND | DOSE % | 2 | 4 | 6 | 24 |
|---|---|---|---|---|---|
| Example 1 | 0.01 | −0.1 ± 0.8 | −5.2 ± 1.4** | −4.3 ± 0.8 | −4.4 ± 0.8 |
| Example 1 | 0.1 | −3.1 ± 0.8** | −3.2 ± 0.7 | −2.7 ± 0.8 | — |
| Example 3 | 0.01 | −2.2 ± 1.0* | 5.5 ± 1.1** | −4.0 ± 1.4* | 2.7 ± 1.1* |
| Example 3 | 0.1 | −1.3 ± 0.4* | 2.3 ± 0.7** | −2.6 ± 0.6** | — |
| Example 5 | 0.1 | −2.7 ± 0.8* | −3.4 ± 0.9* | −2.8 ± 0.4** | −2.1 ± 1.6* |
| Example 4 | .01 | −0.9 ± 0.7 | −2.5 ± 0.7* | −3.2 ± 0.7** | −1.3 ± 0.7 |
| Fluprostenol | 0.1 | −1.3 ± 0.1 | −2.1 ± 1.1 | −2.7 ± 1.3 | −3.1 ± 0.9* | n = 8,
*p < 0.05,
**p < 0.01.

Example 7

Measurement of ocular surface hyperemia was visually assessed and scored according to the following schematic:

| Hyperemia Score | Assigned Value |
|---|---|
| <1 | 1 |
| 1 slight | 2 |
| >1 <2 | 3 |
| 2 moderate | 4 |
| >2 >3 | 5 |
| 3 severe | 6 |

(baseline scores for dogs are typically <1)

The hyperemia value for each dog at a single time point (x) is obtained as follows: (treated eye value at hr x-baseline value)−(control eye value at hr x-baseline value). A composite value is then obtained by dividing the sum of the post-treatment measurement at each time point by the number of animals in the group: i.e. m where m=n measurements of ocular surface hyperemia. Ocular surface hyperemia is evaluated at the same time points as intraocular pressure measurement. It should be noted that untreated dog eyes frequently have a pink/red tone. Thus, values of <1 and 1 are essentially within the normal range. The results are reported in Table 2, below.

TABLE 2

Comparison of effects of certain compounds of the invention on dog ocular surface hyperemia.

| COMPOUND | DOSE % | OCULAR SURFACE HYPEREMIA: COMPOSITE SCORE |
|---|---|---|
| Example 1 | 0.01 | — |
| Example 1 | 0.1 | 0.33 |
| Example 3 | 0.01 | — |
| Example 3 | 0.1 | 0.81 |
| Example 5 | 0.1 | 0.81 |
| Example 4 | 0.01 | 1.08 |
| Fluprostenol | 0.1 | 1.50 |

Values are composite scores as indicated in the methods.

It is clear that the compounds of Examples 1, 3 and 5, unexpectedly, show better efficacy at lowering IOP than Example 4 while showing less hyperemia.

The compounds of the invention may also be useful in the treatment of various pathophysiological diseases including acute myocardial infarction, vascular thrombosis, hypertension, pulmonary hypertension, ischemic heart disease, congestive heart failure, and angina pectoris, in which case the compounds may be administered by any means that effect vasodilation and thereby relieve the symptoms of the disease. For example, administration may be by oral, transdermal, parenterial, subcutaneous, intravenous, intramuscular, intraperitoneal, transdermal, or buccal routes.

The compounds of the invention may be used alone, or in combination with other of the known vasodilator drugs.

The compounds of the invention may be formulated into an ointment containing about 0.10 to 10% of the active ingredient in a suitable base of, for example, white petrolatum, mineral oil and petroatum and lanolin alcohol. Other suitable bases will be readily apparent to those skilled in the art.

The pharmaceutical preparations of the present invention are manufactured in a manner which is itself known, for example, by means of conventional dissolving or suspending the compounds, which are all either water soluble or suspendable. For administration in the treatment of the other mentioned pathophysiological disorders. The pharmaceutical preparations which can be used orally include push-fit capsules made of gelatin, as well as soft, sealed capsules make of gelatin and a plasticizer such as glycerol or sorbitol. The push-fit capsules can contain the active compounds in liquid form that may be mixed with fillers such as lactose, binders such as starches, and/or lubricants such as talc or magnesium stearate and, optionally, stabilizers. In soft capsules, the active compounds are preferably dissolved or suspended in suitable liquids, such as in buffered salt solution. In addition, stabilizers may be added.

In addition to being provided in a liquid form, for example in gelatin capsule or other suitable vehicle, the pharmaceutical preparations may contain suitable excipients to facilitate the processing of the active compounds into preparations that can be used pharmaceutically. Thus, pharmaceutical preparations for oral use can be obtained by adhering the solution of the active compounds to a solid support, optionally grinding the resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as inders such as starch, paste using for example, maize starch, wheat starch, rich starchy, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, crosslinked polyvinyl pyrrolidone, agar, or algenic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which if desired, are resistant to gastric juices. For this purpose, concentrated sugar solutions may be used, which may optionally containing gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tables or dragee coatings, for example, for identification or in order to characterize combinations of active compound doses.

Suitable formulations for intravenous or parenteral administration include aqueous solutions of the active compounds. In addition, suspensions of the active compounds as oily injection suspensions may be administered. Aqueous injection suspensions may contain substances which increase the viscosity of the suspension include, for example, sodium carboxymethyl cellulose, soribitol, and/or dextran. Optionally, the suspension may also contain stabilizers.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. For example, the present invention contemplates certain prodrugs of the above disclosed compounds, wherein $R^4$ is These compounds may be made by acylation or esterification of the corresponding hydroxy or amino derivative. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

The invention claimed is:

1. A pharmaceutical composition comprising cyclopentane N-ethyl hepteneamide-5-cis-2-(3α-hydroxy-5-phenyl-1-trans-pentenyl)-3, 5-dihydroxy, $[1_\alpha 2_\beta 3_\alpha 5_\alpha]$, benzalkonium chloride, and sodium chloride as a tonicity agent.

2. The pharmaceutical composition of claim 1, wherein the composition is for ophthalmic application.

3. The pharmaceutical composition of claim 2, wherein the composition is packaged in a dropper for ophthalmic application.

4. The pharmaceutical composition of claim 1, wherein the pH of the composition is 4.5-7.5.

5. The pharmaceutical composition of claim 1, for use in lowering intraocular pressure of the eye.

6. The pharmaceutical composition of claim 1, for treatement of glaucoma.

* * * * *